(12) United States Patent
Fomina et al.

(10) Patent No.: US 10,948,413 B2
(45) Date of Patent: Mar. 16, 2021

(54) FLUOROPHORE MULTIPLEXING VIA PH MODULATION

(71) Applicant: Robert Bosch GmbH, Stuttgart (DE)

(72) Inventors: Nadezda Fomina, Redwood City, CA (US); Habib Ahmad, Sunnyvale, CA (US); Christopher Johnson, San Carlos, CA (US); Christoph Lang, Sunnyvale, CA (US); Patrick Staley, Sunnyvale, CA (US); Juergen Steigert, Stuttgart (DE); Franz Laermer, Weil der Stadt (DE)

(73) Assignee: ROBERT BOSCH GMBH, Stuttgart (DE)

( * ) Notice: Subject to any disclaimer, the term of this patent is extended or adjusted under 35 U.S.C. 154(b) by 34 days.

(21) Appl. No.: 15/851,146

(22) Filed: Dec. 21, 2017

(65) Prior Publication Data
US 2019/0195796 A1 Jun. 27, 2019

(51) Int. Cl.
*G01N 21/64* (2006.01)
*C12Q 1/68* (2018.01)
(Continued)

(52) U.S. Cl.
CPC ......... *G01N 21/6428* (2013.01); *C12M 23/16* (2013.01); *C12Q 1/68* (2013.01);
(Continued)

(58) Field of Classification Search
CPC .... G01N 21/6428; G01N 21/64; G01N 21/63; G01N 21/62; C12M 23/16; C12M 23/02; C12M 23/00; C12Q 1/68; C12Q 1/00
(Continued)

(56) References Cited

U.S. PATENT DOCUMENTS

| 5,998,135 A | * | 12/1999 | Rabbani | ................. C07H 21/00 |
|---|---|---|---|---|
| | | | | 435/6.11 |
| 2016/0003766 A1 | | 1/2016 | Johnson et al. | |
| 2017/0008825 A1 | * | 1/2017 | Johnson | ................. C12Q 1/001 |

FOREIGN PATENT DOCUMENTS

| GB | 2266182 A | 10/1993 |
|---|---|---|
| WO | 03/043402 A2 | 5/2003 |

OTHER PUBLICATIONS

Savoy S. et al.: "Solution-Based Analysis of Multiple Analytes by A Sensor Array: Toward the Development on an "Electronic Tongue"", Visual Communications and Image Processing; Jan. 20, 2004-Jan. 20, 2004; San Jose, vol. 3539, Nov. 1, 1998, pp. 17-26.
Gracie K. et al.: Interaction of Fluorescent Dyes with DNA and Spermine Using Fluorescence Spectroscopy, The Analyst, vol. 139, No. 15, May 22, 2014, pp. 3735-3743.
Schuler et al., "Monochrom Multiplexing in Polymerase Chain Reaction by Photobleaching of Fluorogenic Hydrolysis Probes", Analytical Chemistry 2016, 88 (5), pp. 2590-2595.
(Continued)

*Primary Examiner* — Christine T Mui
(74) *Attorney, Agent, or Firm* — Norton Rose Fulbright US LLP; Gerard Messina (57) ABSTRACT

An apparatus to detect more than one analyte in a solution comprising at least one electrode in contact with the solution, at least two dyes including a first dye and a second dye, and an electrochemically active agent, where the solution has a pH, the electrode is configured to modulate the pH of the solution by oxidizing or reducing the electrochemically active agent, the first dye and the second dye fluoresce at different pH levels, fluorescence of the first dye is used to indicate the presence of a first analyte, and fluorescence of the second dye is used to indicate the presence of a second analyte. Methods of detecting multiple analytes in a solution are also provided.

18 Claims, 4 Drawing Sheets
(3 of 4 Drawing Sheet(s) Filed in Color)

(51) Int. Cl.
  *C12M 3/06*     (2006.01)
  *G01N 33/533*   (2006.01)
  *G01N 33/58*    (2006.01)
  *C12Q 1/6825*   (2018.01)
  *G01N 33/543*   (2006.01)

(52) U.S. Cl.
  CPC ....... *C12Q 1/6825* (2013.01); *G01N 21/6486* (2013.01); *G01N 33/533* (2013.01); *G01N 33/5438* (2013.01); *G01N 33/582* (2013.01); *G01N 2021/6441* (2013.01)

(58) Field of Classification Search
  USPC .................................................. 436/150, 149
  See application file for complete search history.

(56) References Cited

OTHER PUBLICATIONS

Arrigan et al., "Electrochemical strategies for the label-free detection of amino acids, peptides and proteins", Analyst, 2007, 132, pp. 615-632.

Martinez et al., "Fluorescent pH probes, Fluorescent Proteins, and Intrinsic Cellular Fluorochromes re Tools to Study Cytosolic pH (pHcyt) in Mammalian Cells", Biomarkers and Biological Spectral Imaging, Gregory H. Bearman, Darryl J. Bornhop, Richard M. Levenson, Editors, Proceedings of SPIE, vol. 4259 (2001), pp. 144-156.

Han et al., "Fluorescent Indicators for Intracellular pH", Chemical Reviews 2010, 110, pp. 2709-2728.

\* cited by examiner

| Dye | Optimal pH | Abs, $\lambda_{max}$ (nn) | Em, $\lambda_{max}$ (nn) | Channel |
|---|---|---|---|---|
| ATTO 488 | not ph-sens | 500 | 520 | 1 |
| LysoSensor Green | acidic | 445 | 520 | 1 |
| FAM | neutral | 496 | 526 | 1 |
| pH rodo | acidic | 550 | 585 | 2 |
| ATTO 550 | not ph-sens | 554 | 576 | 2 |
| TAMRA | not ph-sens | 543 | 571 | 2 |
| Rhodamine B derivatives | acidic | 560 | 590 | 2 |
| ROX | not ph-sens | 568 | 591 | 2 |
| SNARF | basic | 534 | 645 | 3 |
| ATTO 633 | not ph-sens | 633 | 651 | 3 |
| naphtafluorescein | basic | 595 | 670 | 4 |
| Cy5 | not ph-sens | 649 | 670 | 4 |

FLUOROPHORE MULTIPLEXING VIA PH MODULATION

FIELD OF THE INVENTION

Aspects of the present invention relate to an apparatus and a method for detecting multiple analytes in a solution.

BACKGROUND

Multiplexing is a technique widely used to save cost via decreased reagent consumption and increased throughput and when dealing with precious samples. This technique is beneficial in applications that analyze biopsy samples, such as polymerase chain reaction (PCR), fluorescence in situ hybridization (FISH) to detect specific DNA or RNA targets in single cells or tissue samples, and fluorescent antibody assays. In these applications, the degree of multiplexing is usually limited by the number of fluorescent probes with non-overlapping spectral properties and the number of optical channels available on an analytical instrument.

For example, in general, the number of reactions that can be detected simultaneously in one PCR tube is limited to five, primarily because PCR instruments can detect no more than four or five color channels, one of which may be reserved as a reference channel. Real-time quantitative PCR (qPCR) can detect 4 to 5 analytes at once by reading out fluorescence from 4 to 5 different dyes with non-overlapping spectral properties. One strategy to expand the number of analytes per channel combines fluorophores with the same emission maxima but different fluorescent stability towards photobleaching. See Schuler et al., F. Anal. Chem. 2016, 88 (5), 2590-2595. However, this technique allows only end-point detection, since photobleaching is an irreversible process, and is therefore not suitable for qPCR. Other strategies utilize changing the pH of biological solutions through buffer exchange, desalting, or dialysis. However, all of these approaches lead to some sample loss or dilution, are time-consuming, and are not amenable to repeated incorporation into a qPCR process.

SUMMARY

A summary of certain example embodiments of the present invention is set forth below. It should be understood that these aspects are presented merely to provide the reader with a brief summary of these certain embodiments and that these aspects are not intended to limit the scope of the present invention. Indeed, this invention can encompass a variety of aspects that may not be set forth below.

Example embodiments of the present invention increase the number of fluorescent probes that can be distinguished in a single sample by taking advantage of pH-dependent fluorescent properties of organic dyes. If two dyes fluoresce at the same wavelength (i.e., have overlapping spectral properties), but have distinctly different pH profiles (for example, one has higher fluorescence in acidic or basic pH, while another one has either the reverse pH behavior or is insensitive to pH changes), then both fluorophores can be detected using the same detector (i.e., channel) by measuring the signal at two different pHs. Modulating fluorescence of dyes by changing the solution pH can extend the number of targets detectable within the same number of channels.

Example embodiments of the present invention utilize a pH modulation step that is quick, reversible, repeatable, and does not require an exchange of solutions in order to preserve the concentrations of the essential components required for qPCR (e.g., nucleotides, salts, primers, polymerase, fluorescently labeled probes, and DNA), except for the concentrations of hydronium, hydroxyl, and/or buffer ions. Example embodiments of the present invention utilize electrochemical pH modulation, where the concentration of hydronium ions is altered in situ as the result of a controlled electrochemical reaction (oxidation or reduction) occurring at the surface of an electrode in contact with qPCR solution. This approach allows for dynamic control over solution pH, is reversible, and can be repeated multiple times throughout the qPCR process after an initial one-time addition of electroactive reagents. The potential at which the electrochemical reaction occurs is low enough to prevent any other components of qPCR process from undergoing electrochemical changes. This limit is mainly defined by the stability of amino acids and nucleotides towards oxidation/reduction. See Arrigan, D. W. M. 2007, 132, 615-632. Another limitation is chemical compatibility of electroactive reagents with components of qPCR.

U.S. Pat. No. 9,810,688 describes an electrochemical pH-modulation platform that provides dynamic, on-demand control over the solution pH. Combined with a microfluidic environment, this pH modulation technology can be used to alter the pH throughout the solution inside a microfluidic channel.

In example embodiments of the present invention, in the case of an end-point PCR reaction, the pH needs to be changed only once at the end of the amplification process in order to expand the number of targets detectable within the same channel, and this step is not required to be reversible.

In example embodiments of the present invention, in the case of real-time quantitative PCR (qPCR), the pH is to be changed after each amplification cycle in order to construct an amplification curve, and therefore this step is to be reversible. Incorporating a pH modulation step at the point of read-out expands the number of dyes that can be detected independently by removing the requirement that the dyes have non-overlapping spectral properties. The use of multiple dyes with overlapping absorption and emission spectra but different pH profiles allows detection of more analytes in one pot without altering the existing detection instruments (same light sources and filters can be used for readout). The dyes that are conventionally used for qPCR and readily available commercially can be used in this approach.

According to example embodiments, an apparatus to detect more than one analyte in a solution includes: (a) at least one electrode in contact with the solution; (b) at least two dyes, including a first dye and a second dye; and (c) an electrochemically active agent; where the solution has a pH, the electrode is configured to modulate the pH of the solution by oxidizing or reducing the electrochemically active agent, the first dye and the second dye fluoresce at different pH levels, fluorescence of the first dye is used to indicate the presence of a first analyte, and fluorescence of the second dye is used to indicate the presence of a second analyte.

In some example embodiments, the electrochemically active agent is a quinone.

In some example embodiments, the first dye exhibits higher fluorescence in acidic pH than the second dye, and the second dye exhibits higher fluorescence in neutral or basic pH than the first dye.

In some example embodiments, the first dye exhibits higher fluorescence in basic pH than the second dye, and the second dye exhibits higher fluorescence in acidic or neutral pH than the first dye.

In some example embodiments, the first dye is selected from a group consisting of LysoSensor Green, FAM, pH rodo, rhodamine B derivatives, SNARF, ATTO 488, ATTO 633, TAMRA, ATTO 550, ROX, naphtafluorescein, and Cy5.

In some example embodiments, the apparatus includes multiple dyes, where each dye fluoresces at different pH levels, and where fluorescence of each dye is used to indicate the presence of a different analyte.

In some example embodiments, the apparatus is contained within a channel of an analytic instrument.

In some example embodiments, the electrode is platinum, gold, silver, indium tin oxide, fluorine doped tin oxide, glassy carbon, or graphite.

According to example embodiments, a method of detecting multiple analytes in a solution, where the solution includes an electrochemically active agent and at least two dyes including a first dye and a second dye, includes: (a) applying a current or voltage to an electrode in a solution having a pH; (b) oxidizing or reducing the electrochemically agent to change the pH of the solution to a first pH; (c) measuring a fluorescence of the first dye at the first pH, indicating the presence of a first analyte; (d) oxidizing or reducing the electrochemically agent to change the pH of the solution to a second pH; and (e) measuring a fluorescence of the second dye at the second pH, indicating the presence of a second analyte.

In some example embodiments, the first dye exhibits higher fluorescence in acidic pH than the second dye, and the second dye exhibits higher fluorescence in neutral or basic pH than the first dye.

In some example embodiments, the first dye exhibits higher fluorescence in basic pH than the second dye, and the second dye exhibits higher fluorescence in acidic or neutral pH than the first dye.

In some example embodiments, the first dye is selected from a group consisting of LysoSensor Green, FAM, pH rodo, rhodamine B derivatives, SNARF, ATTO 488, ATTO 633, TAMRA, ATTO 550, ROX, naphtafluorescein, and Cy5.

In some example embodiments, the solution further includes multiple dyes, wherein each dye fluoresces at different pH levels, and wherein fluorescence of each dye is used to indicate the presence of a different analyte.

In some example embodiments, detection of the multiple analytes occurs within a channel of an analytic instrument.

According to example embodiments, an apparatus includes: (a) a fluorescence sensor; (b) a control unit including processing circuitry; (c) a receptacle configured to hold within the receptacle a solution including a plurality of analytes with respective dyes and including an electrochemically active agent; (d) and at least one electrode arranged relative to the receptacle such that, when the receptacle holds the solution, the at least one electrode is in contact with the solution; where the processing circuitry is configured to: (i) control the at least one electrode to at least one of oxidize and reduce the electrochemically active agent, thereby modulating a pH of the solution; (ii) obtain from the fluorescence sensor, at each of a plurality of pH levels of the solution attained by the modulation, a respective fluorescence signal indicating a fluorescence of the solution caused by respective ones of the dyes at the respective pH levels; (iii) identify respective ones of the analytes included in the solution based on the obtained fluorescence signals and associations of respective ones of the obtained fluorescence signals with respective ones of the plurality of pH levels; and (iv) output the identifications.

In some example embodiments, the solution is arranged in the receptacle, where the dyes include a first dye and a second dye that fluoresce at different ones of the pH levels.

Although various aspects of the example embodiments of the present invention may be described independently, combinations of the example embodiments are understood to be referred to herein. In addition, and conversely, it should be understood that although a feature may be described in the context of a combination with other features, the different features are separable and do not necessarily require or rely on one another for a functional or useful embodiment of the present invention.

The aspects and embodiments described in the foregoing are presented merely to provide a brief summary of these example embodiments, and aspects and embodiments aspects are not intended to limit the scope of this disclosure. Indeed, the present invention may also encompass a variety of other aspects. These and other features, aspects, and advantages of the present invention are further clarified by the following detailed description of certain exemplary embodiments in view of the accompanying drawings throughout which like characters represent like parts.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

DETAILED DESCRIPTION

Example embodiments of the present invention utilize pH-dependent fluorescent properties of dyes to enable multiplexing in combination with the ability to dynamically change solution pH. According to example embodiments, dyes with matching excitation/emission properties can be imaged in the same instrument channel, increasing the number of analytes that can be detected in a single reaction within the existing number of optical channels.

Most commonly used PCR dyes are fluorescein derivatives (such as JOE, TET, HEX, and FAM), rhodamine derivatives (ROX, TAMRA), and cyanine dyes (Cy-3, Cy-5). The fluorescent properties of these dyes are affected by the pH of the surrounding solution. For example, fluorescein derivatives show maximum fluorescence in neutral pH, while their fluorescence decreases dramatically in acidic environment. See Martinez et al., Biomarkers and Biological Spectral Imaging, 2(16), 144-156 (2001). On the other hand, cyanine dyes and rhodamine derivatives show maximum fluorescence in acidic pH. See Han et al., Fluorescent Indicators for Intracellular pH. Chemical Reviews, 110, 2709-2728 (2010). ATTO dyes are a new class of qPCR dyes whose fluorescence is independent of pH changes within the range of biologically relevant values.

Figure 1:
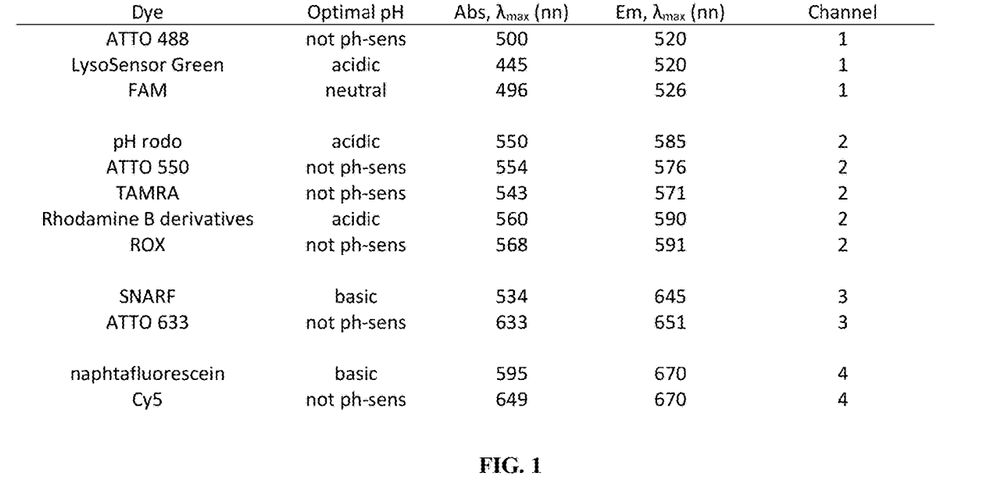
FIG. 1 shows a table showing examples of dye combinations for detection of increased number of analytes.
Figure 2:
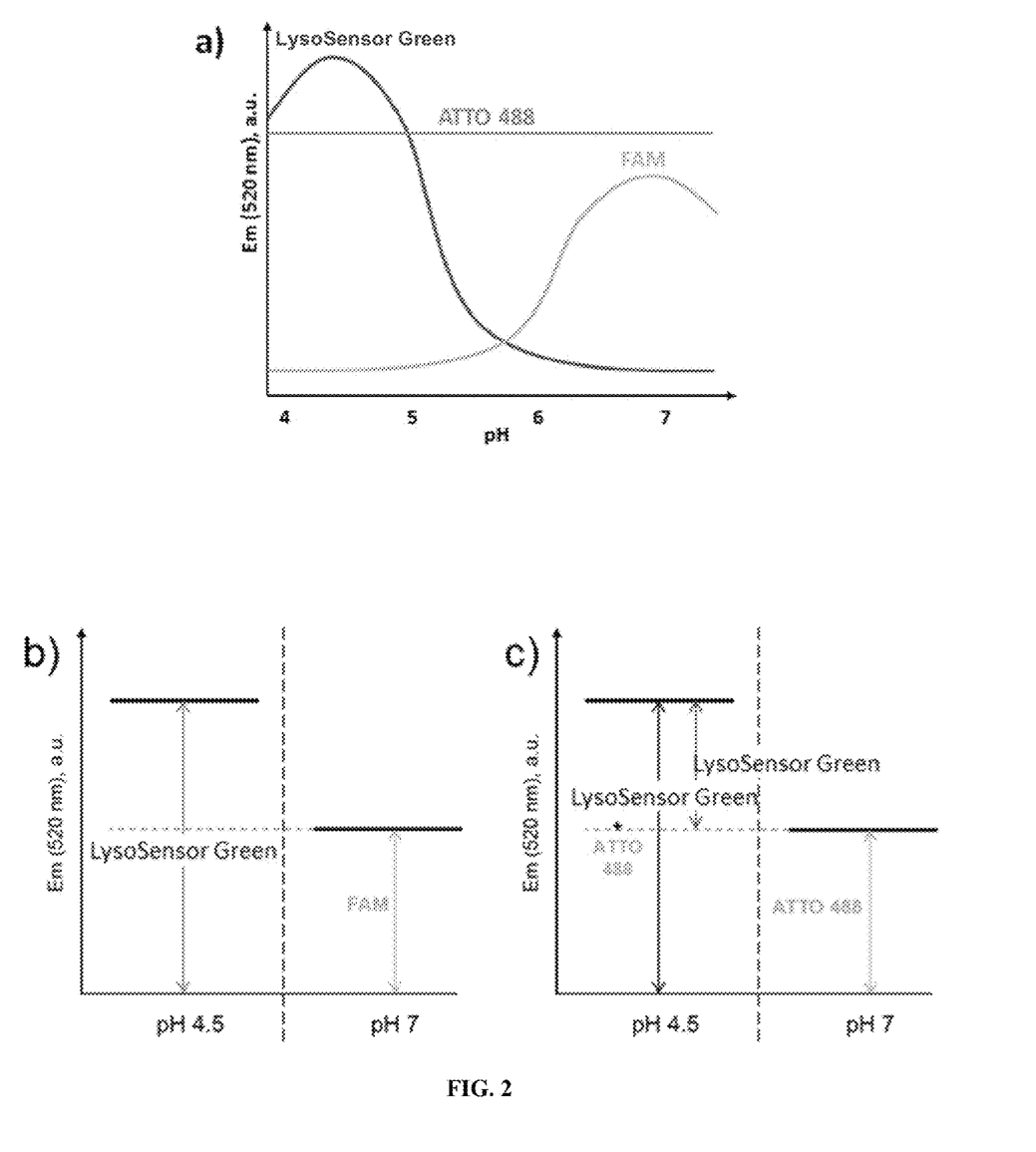
FIG. 2 is a schematic illustration of deconvolution of signals from two dyes in a single channel through pH modulation.

In example embodiments of the present invention, in order to deconvolute the contribution of each dye, fluorescence is recorded at different pHs. Some possible dye combinations are summarized in FIG. 1. For example, LysoSensor Green, FAM, and ATTO 488 have peak absorption and emission in the green region of the spectrum. However, LysoSensor Green has optimal fluorescence in acidic pH, while its fluorescence is quenched in neutral or basic pH, and FAM dye displays the inverse pH-dependent behavior. In contrast, ATTO 488 has fluorescence independent of pH (FIG. 2, part (a)). Therefore, LysoSensor Green can be combined with FAM in the same channel. In acidic pH, fluorescence of FAM will be quenched while the fluorescence of LysoSensor Green will be measured; in neutral pH, fluorescence of LysoSensor Green will be quenched, allowing for measurement of FAM signal (FIG. 2, part (b)). Alternatively, LysoSensor Green can be combined with ATTO 488. In this case, in acidic pH, the measured fluorescence signal will be the sum of LysoSensor Green plus ATTO 488, while, in neutral pH, only ATTO 488 will be measured (FIG. 2, part (c)). The contribution of LysoSensor Green can be obtained as a difference of fluorescent intensities at acidic and neutral pHs.

Following the same principle, FAM can be combined with ATTO 488; pH rodo and rhodamine B derivatives can both be combined with ATTO 550, TAMRA, or ROX; ATTO 633 can be combined with SNARF; and naphthofluorescein can be combined with Cy5. These examples are not limiting, since any two or more dyes that have compatible spectral properties (i.e., can be excited at the same wavelength and their fluorescence can be read out at the same wavelength) but distinctly different pH profiles can be used in the same fashion.

In example embodiments of the present invention, in order to quantitatively determine the contribution of each dye to the aggregate signal (and therefore the concentration of each analyte), calibration curves are constructed for each individual component at each sampled pH, since the dye's extinction coefficient and fluorescence intensity will be affected by pH. Optimal pH values for sampling can be determined by constructing the pH profiles of each dye and determining the values at which the fluorescence intensities are most different.

In example embodiments of the present invention, rapid and repeatable change in pH can be achieved via a reversible electrochemical oxidation/reduction reaction that results in the production or consumption of hydronium or hydroxyl ions:

In example embodiments of the present invention, electroactive molecules capable of electrochemical oxidation or reduction reaction that results in generation or consumption of protons are used. For example, any quinone derivative, hydrazine derivative, or phenol-Ru(2,2'-bipyridine)$_3^{2+}$) can be used. Examples of such reactions are oxidation or reduction of quinone derivatives (as described in U.S. Ser. No. 14/792,553), hydrazine derivatives, or water. The pH range using quinone derivatives is from about 4 to about 10. There is no theoretical limit for pH that can be generated through this method on the acidic end, while on the basic end it is defined by the pKa of the specific quinone derivative employed.

Figure 3:
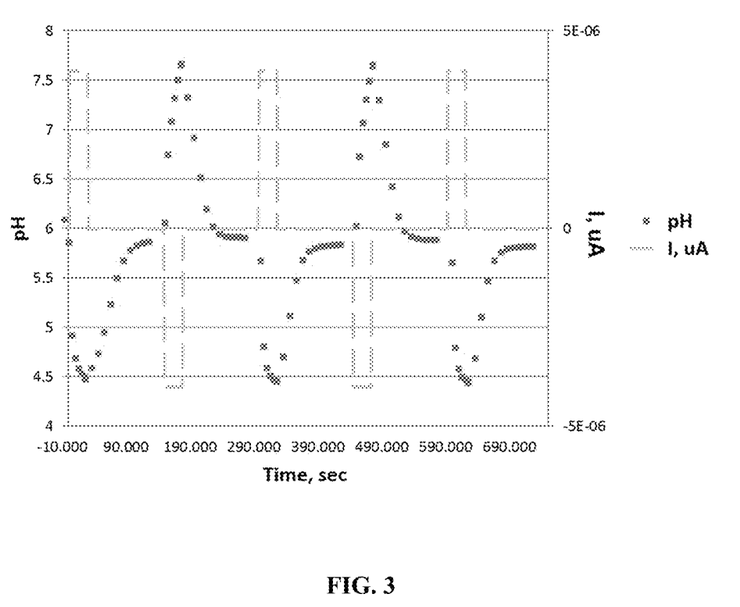
FIG. 3 illustrates pH changes in a solution via oxidation/reduction of quinones.

FIG. 3 demonstrates changing the pH of a solution via oxidation/reduction of quinones. Specifically, FIG. 3 demonstrates the repeatability of pH change as the result of oxidation of 2,5-dimethylhydroquinone on indium-tin oxide electrode in 1 mM phosphate buffer. The pH values were determined by measuring the fluorescent signal of the pH-responsive probe Green Fluorescent Protein. When anodic current is applied to the electrode immersed in a buffered solution containing 2,5-dimethylhydroquinone, the produced protons overcome the buffer and pH of the solution becomes more acidic. Application of cathodic current leads to alkalinisation of the solution as the result of the reverse reaction-reduction of 2,5-dimethylbenzoquinone and consumption of protons.

Figure 4:
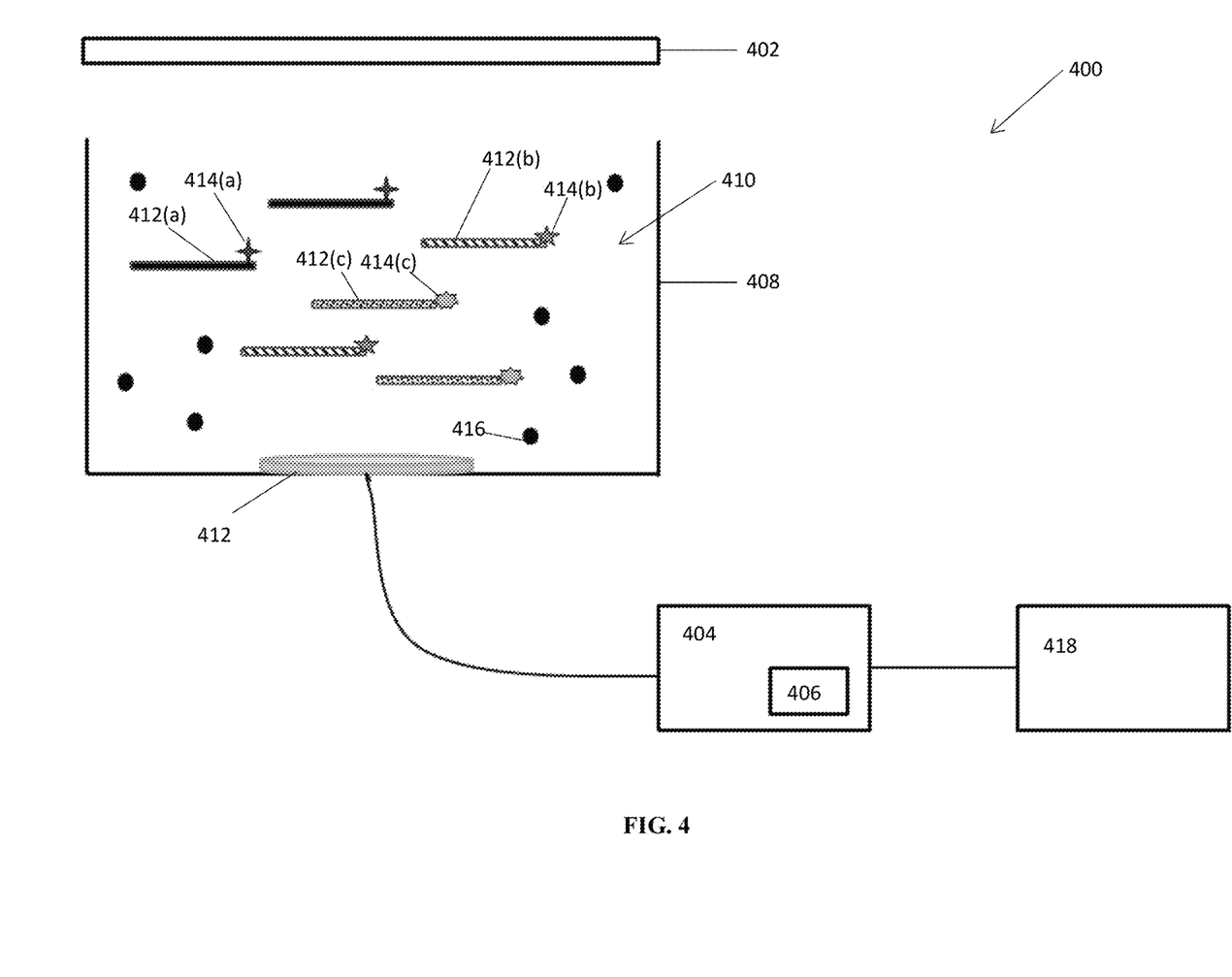
FIG. 4 illustrates a device according to an example embodiment.

FIG. 4 shows apparatus 400 that includes fluorescence sensor 402, control unit 404 that includes processing circuitry 406, receptacle 408 containing solution 410, and electrode 412 in contact with solution 410. Solution 410 includes analytes 412(a), 412(b), and 412(c), each with respective dye 414(a), 414(b), and 414(c), and electrochemically active agent 416. Processing circuitry 406 is configured to control electrode 412 to either oxidize or reduce electrochemically active agent 416, thus modulating the pH of solution 410. Dyes 414(a), 414(b), and 414(c) fluoresce at different pH levels of solution 410, each giving a fluorescence signal at a certain pH level, indicating the presence of analytes 412(a), 412(b), and 412(c), respectively. Fluorescence sensor 402 detects these fluorescence signals of dyes 414(a), 414(b), and 414(c) and relays such signals to processing circuitry 406, which identifies analytes 412(a), 412(b), and 412(c) in solution 410 based on the obtained fluorescence signals and associations of the signals with certain pH levels. Processing circuitry 406 outputs the identifications of analytes 412(a), 412(b), and 412(c) to display unit 418.

An example embodiment of the present invention is directed to one or more processors, which can be implemented using any conventional processing circuit and device or combination thereof, e.g., a Central Processing Unit (CPU) of a Personal Computer (PC) or other workstation processor, to execute code provided, e.g., on a hardware non-transitory computer-readable medium including any conventional memory device, to perform any of the methods described herein, alone or in combination, e.g., for control of the electrode and/or analysis of fluorescence signals. The one or more processors can be embodied in a server or user terminal or combination thereof. The user terminal can be embodied, for example, a desktop, laptop, hand-held device, Personal Digital Assistant (PDA), television set-top Internet appliance, mobile telephone, smart phone, etc., or as a combination of one or more thereof. The memory device can include any conventional permanent and/or temporary memory circuits or combination thereof, a non-exhaustive list of which includes Random Access Memory (RAM), Read Only Memory (ROM), Compact Disks (CD), Digital Versatile Disk (DVD), and magnetic tape. Such devices can be used for navigating pages along parallel history branches and/or for redoing edits along parallel redo branches.

An example embodiment of the present invention is directed to one or more hardware computer-readable media, e.g., as described above, having stored thereon instructions executable by a processor to perform the various methods described herein, each alone or in combination.

An example embodiment of the present invention is directed to a method, e.g., of a hardware component or machine, of transmitting instructions executable by a processor to perform the methods described herein, alone or in combination.

The embodiments described above, which have been shown and described by way of example, and many of their advantages will be understood by the foregoing description, and it will be apparent that various changes can be made in the form, construction and arrangement of the components without departing from the disclosed subject matter or without sacrificing one or more of its advantages. Indeed, the described forms of these embodiments are merely explanatory. These embodiments are susceptible to various modifications and alternative forms, and the following listing of claims is not intended to exclude any such changes and the embodiments are not to be limited to the particular forms disclosed, but rather to cover all modifications, equivalents, and alternatives falling with the spirit and scope of this disclosure.

That is, the above description is intended to be illustrative, and not restrictive, and is provided in the context of a particular application and its requirements. Those skilled in the art can appreciate from the foregoing description that the present invention may be implemented in a variety of forms, and that the various embodiments may be implemented alone or in combination. Therefore, while the embodiments of the present invention have been described in connection with particular examples thereof, the general principles defined herein may be applied to other embodiments and applications without departing from the spirit and scope of the described embodiments, and the true scope of the embodiments and/or methods of the present invention are not be limited to the embodiments shown and described, since various modifications will become apparent to the skilled practitioner upon a study of the drawings, specification, and following claims. For example, components and functionality may be separated or combined differently than in the manner of the various described embodiments, and may be described using different terminology. These and other variations, modifications, additions, and improvements may fall within the scope of the disclosure as defined in the claims that follow.

What is claimed is:

1. An apparatus to detect a plurality of analytes in a solution, the apparatus comprising:
   at least one electrode in contact with the solution;
   at least two dyes, including a first dye and a second dye; and
   an electrochemically active agent that is a quinone and not immobilized within the apparatus;
   wherein:
      the solution has a pH;
      the electrode is configured to modulate the pH of the solution by oxidizing or reducing the electrochemically active agent to generate or consume protons in a pH range of 4 to 10;
      the first dye and the second dye fluoresce at different pH levels;
      fluorescence of the first dye is used to indicate presence of a first analyte; and
      fluorescence of the second dye is used to indicate presence of a second analyte.

2. The apparatus of claim 1, wherein the first dye exhibits higher fluorescence in acidic pH than the second dye.

3. The apparatus of claim 2, wherein the second dye exhibits higher fluorescence in neutral pH than the first dye.

4. The apparatus of claim 2, wherein the second dye exhibits higher fluorescence in basic pH than the first dye.

5. The apparatus of claim 1, wherein the first dye exhibits higher fluorescence in neutral pH than the second dye, and the second dye exhibits higher fluorescence in basic pH than the first dye.

6. The apparatus of claim 1, wherein the first dye is selected from a group consisting of LysoSensor Green, FAM, pH rodo, rhodamine B derivatives, SNARF, ATTO 488, ATTO 633, TAMRA, ATTO 550, ROX, naphtafluorescein, and Cy5.

7. The apparatus of claim 1, wherein each of the dyes fluoresces at different pH levels, and fluorescence of each dye is used to indicate the presence of a different analyte.

8. The apparatus of claim 1, wherein the apparatus is contained within a channel of an analytic instrument.

9. The apparatus of claim 1, wherein the electrode is platinum, gold, silver, indium tin oxide, fluorine doped tin oxide, glassy carbon, or graphite.

10. A method of detecting a plurality of analytes in a solution, wherein the solution comprises an electrochemically active agent that is a quinone and at least two dyes including a first dye and a second dye, wherein the first dye and the second dye fluoresce at different pH levels, the method comprising:
    obtaining the apparatus of claim 1;
    using the apparatus of claim 1 to apply a current or voltage to the at least one electrode in contact with a solution having a pH and to oxidize or reduce the electrochemically active agent that is not immobilized within the apparatus to change the pH of the solution to a first pH;
    measuring a fluorescence of the first dye at the first pH, indicating the presence of the first analyte;
    using the apparatus to oxidize or reduce the electrochemically active agent to change the pH of the solution to a second pH; and
    measuring a fluorescence of the second dye at the second pH, indicating the presence of the second analyte.

11. The method of claim 10, wherein the first dye exhibits higher fluorescence in acidic pH than the second dye.

12. The method of claim 11, wherein the second dye exhibits higher fluorescence in neutral pH than the first dye.

13. The method of claim 11, wherein the second dye exhibits higher fluorescence in basic pH than the first dye.

14. The method of claim 10, wherein the first dye exhibits higher fluorescence in neutral pH than the second dye, and the second dye exhibits higher fluorescence in basic pH than the first dye.

15. The method of claim 10, wherein the first dye is selected from a group consisting of LysoSensor Green, FAM, pH rodo, rhodamine B derivatives, SNARF, ATTO 488, ATTO 633, TAMRA, ATTO 550, ROX, naphtafluorescein, and Cy5.

16. The method of claim 10, wherein detection of the multiple analytes occurs within a channel of an analytic instrument.

17. The apparatus of claim 1, further comprising:
    a fluorescence sensor;
    a control unit including processing circuitry; and
    a receptacle configured to hold the solution within the receptacle;
    wherein:
       the solution comprises a plurality of analytes, the at least two dyes and the electrochemically active agent;

the at least one electrode is arranged relative to the receptacle such that, when the receptacle holds the solution, the at least one electrode is in contact with the solution; and the processing circuitry is configured to:
control the at least one electrode to at least one of oxidize and reduce the electrochemically active agent, thereby modulating a pH of the solution;
obtain from the fluorescence sensor, at each of a plurality of pH levels of the solution attained by the modulation, a respective fluorescence signal indicating a fluorescence of the solution caused by respective ones of the dyes at the respective pH levels;
identify respective ones of the analytes included in the solution based on the obtained fluorescence signals and associations of respective ones of the obtained fluorescence signals with respective ones of the plurality of pH levels; and
output the identifications.

18. The apparatus of claim 1, wherein the at least two dyes are not attached to one another.

\* \* \* \* \*